United States Patent
Lal et al.

(10) Patent No.: US 11,530,293 B2
(45) Date of Patent: Dec. 20, 2022

(54) POLYAMIDES AND AMIDOAMINES DERIVED FROM HYDROXYALKYLPOLYAMINES: EPOXY CURING AGENTS WITH IMPROVED PROPERTIES

(71) Applicant: Evonik Operations GmbH, Essen (DE)

(72) Inventors: Gauri Sankar Lal, Whitehall, PA (US); Sudhir Ananthachar, Hillsborough, NJ (US); Stephen Michael Boyce, Bath, PA (US)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/470,510

(22) PCT Filed: Dec. 15, 2017

(86) PCT No.: PCT/US2017/066723
§ 371 (c)(1),
(2) Date: Jun. 17, 2019

(87) PCT Pub. No.: WO2018/118693
PCT Pub. Date: Jun. 28, 2018

(65) Prior Publication Data
US 2020/0123312 A1 Apr. 23, 2020
US 2020/0308339 A2 Oct. 1, 2020

Related U.S. Application Data

(60) Provisional application No. 62/436,193, filed on Dec. 19, 2016.

(51) Int. Cl.
*C08G 59/54* (2006.01)
*C07C 231/02* (2006.01)
*C07C 233/36* (2006.01)
*C08G 59/22* (2006.01)
*C08G 69/28* (2006.01)

(52) U.S. Cl.
CPC ............ *C08G 59/54* (2013.01); *C07C 231/02* (2013.01); *C07C 233/36* (2013.01); *C08G 59/22* (2013.01); *C08G 69/28* (2013.01)

(58) Field of Classification Search
CPC ........ C08G 59/54; C08G 59/22; C08G 69/28; C07C 231/02; C07C 233/36
See application file for complete search history.

(56) References Cited

U.S. PATENT DOCUMENTS

| | | | |
|---|---|---|---|
| 2,574,537 A | 11/1951 | De Groote et al. | |
| 2,705,223 A | 3/1955 | Renfrew et al. | |
| 3,468,904 A | 9/1969 | Kritchevsky | |
| 4,123,402 A * | 10/1978 | Thomassen | C08G 59/184 523/414 |
| 5,283,124 A * | 2/1994 | Fujibayashi | C07C 233/36 523/404 |
| 6,046,282 A * | 4/2000 | Starner | C08G 59/54 525/432 |
| 6,299,785 B1 * | 10/2001 | Shimokawa | H05K 3/06 156/237 |
| 6,500,912 B1 * | 12/2002 | Corley | C08L 63/00 525/531 |
| 2011/0218270 A1 * | 9/2011 | Suter | C08G 69/34 523/400 |
| 2012/0010330 A1 | 1/2012 | Dettloff et al. | |
| 2015/0094400 A1 * | 4/2015 | Zheng | C08G 59/60 523/222 |

FOREIGN PATENT DOCUMENTS

| | | |
|---|---|---|
| CN | 101602854 A | 12/2009 |
| EP | 0134970 A1 | 3/1985 |
| EP | 0296505 A1 * | 12/1988 |
| GB | 2031431 A | 4/1980 |
| JP | 2012121997 A * | 6/2012 |
| KR | 20130096825 A | 9/2013 |

OTHER PUBLICATIONS

J. G. Dorsey et al., "Determination of the Epoxide Equivalent Weight of Glycidyl Ethers by Proton Magnetic Resonance Spectroscopy," 49 Analytical Chemistry 1144 (1977).*
David J. Anneken et al., "Fatty Acids," in 14 Ullmann's Encyclopedia of Industrial Chemistry 73, published online 2006.*
English-language machine translation of JP-2012121997-A, performed on Espacenet, Aug. 11, 2020.*
Ulrich Poth, "Drying Oils and Related Products," 11 Ullmann's Encyclopedia of Industrial Chemistry 621-636, published online 2001. (Year: 2001).*
PCT International Search Report dated Apr. 19, 2018 corresponding to PCT Application No. PCT/US2017/066723 filed Dec. 15, 2017 (6 pages).
Air Products and Chemicals, et al; Epoxy Curing Agents and Modifiers; Oct. 25, 2002; XP055460939; Retrieved from the Internet on Mar. 20, 2018 from http://specialty-additives.evonik.com/product/specialty-additives/Documents/en-ancamine-1769-europe-datasheet.pdf (1 page).
T. E. Breuer, 'Dimer Acids', in J. I. Kroschwitz (ed.), Kirk-Othmer Encyclopedia of Chemical Technology, 4th Ed., Wiley, New York, 1993, vol. 8, pp. 223-237 (15 pages).

* cited by examiner

*Primary Examiner* — Nicholas E Hill
(74) *Attorney, Agent, or Firm* — Andrew H. Chung; Linda S. Li; Jason S. Ngui

(57) ABSTRACT

Polyamide and amidoamine curing agents comprising a selectively modified amine. The selectively modified amine is formed by a substitution reaction between a polyamine and an epoxide, resulting in a multifunctional amine having a hydroxyl substituent. The curing agents are used to form epoxy resins having improved properties when cured.

16 Claims, No Drawings

POLYAMIDES AND AMIDOAMINES DERIVED FROM HYDROXYALKYLPOLYAMINES: EPOXY CURING AGENTS WITH IMPROVED PROPERTIES

This Application is a § 371 national stage of PCT International Application No. PCT/US2017/066723, filed Dec. 15, 2017, which claims the benefit of U.S. Application No. 62/436,193, filed Dec. 19, 2016, the contents of each of which are hereby incorporated by reference in their entirety into this application.

BACKGROUND OF THE INVENTION

The present disclosure is directed to a composition and a method for forming polyamides and amidoamines from selectively modified amines. Polyamide curing agents are utilized extensively in many markets as epoxy curing agents, including coatings, adhesives, composites, and flooring applications. Polyamide curing agents are described herein which are comprised of the reaction products of selectively modified amines and dimerized fatty acid (dimer acid). A certain amount of monomeric fatty acid may also be used to control molecular weight and viscosity.

"Dimerized" or "dimer" or "polymerized" fatty acid refers, generally, to polymerized acids obtained from unsaturated fatty acids. They are described more fully in T. E. Breuer, 'Dimer Acids', in J. I. Kroschwitz (ed.), *Kirk-Othmer Encyclopedia of Chemical Technology*, 4th Ed., Wiley, New York, 1993, Vol. 8, pp. 223-237. Dimer acid is typically prepared by the acid catalyzed oligomerization under pressure of certain monomeric unsaturated fatty acids, which is commonly a tall oil fatty acid (TOFA), but could alternatively be other vegetable acids such as soya acid or cotton acid. Commercial products generally consist of mostly (>70%) dimeric species, with the rest consisting mostly of trimers and higher oligomers, along with small amounts (generally less than 5%) of monomeric fatty acids. Common mono-functional unsaturated C-6 to C-20 fatty acids also employed in making polyamides include TOFA or soya fatty acid or the like.

Several methods for preparation of (poly) amido polyamine and their use as curing agents for epoxy resins are known. For example, U.S. Pat. No. 2,705,223, which is hereby incorporated by reference in its entirety, describes epoxy resins cured with polyamides based on polymeric fatty acids and polyethyleneamines. European Patent EP 134,970, which is hereby incorporated by reference in its entirety, describes similar polyaminoamides. British Patent GB 2,031,431, which is hereby incorporated by reference in its entirety, discloses epoxy resins cured with mixtures of high molecular weight polyoxyalkylene polyamines and N,N'-bis(3-aminopropyl)ethylenediamine. Epoxy resins are available in many viscosities. Commonly employed epoxy resins are those based upon the diglycidyl ether of bisphenol-A (DGEBA), and higher molecular weight oligomers prepared by the advancement of the DGEBA with additional bisphenol-A. Such resins are usually difunctional or slightly less than difunctional, and characterized by their epoxy equivalent weight (EEW). Thus, bisphenol-A derived epoxy resin with an equivalent weight of 180 has a viscosity of about 8500 mPa s (8500 cP). Slightly increasing the EEW to 190 increases the viscosity to about 12,000 mPa s (12,000 cP). At an equivalent weight of 300 or so epoxy resins partially crystallize at a fairly rapid rate to a semi-solid and above an equivalent weight of about 400 they are solids, and thus their viscosities cannot be measured at room temperature.

In the formulation of coatings, it is frequently advantageous to employ higher molecular weight epoxy resins, such as those with equivalent weight of 450 to 550 (known in the industry as Type I resins). High molecular weight resins dramatically decrease the dry-to-touch time of the coating. Furthermore, higher molecular weight epoxy resins yield more flexible and impact resistant coatings than do lower molecular weight epoxy resins. Unfortunately, the high viscosity of the higher molecular weight epoxy resins requires the use of high levels of solvent to achieve a suitable application viscosity.

Improvements desired in the art of polyamide curing agents include lower emissions, lower viscosity, little or no induction time, and a transparent mix with the epoxy resin that can be formed in an economical process that does not suffer from the drawbacks of the prior art. In addition, desired features of the epoxy product include improved surface appearance when applied under adverse conditions, and good gloss and hardness development. There is also a need for polyamides that show less carbamation (blushing) when used in thin film coating applications, increased cure speeds for low temperature curing and improved adhesion to the substrate on which it is applied.

BRIEF SUMMARY OF THE INVENTION

The present disclosure includes polyamide and amidoamine curing agents prepared from amines and fatty acids. At least a portion of the amines are selectively modified. Selectively modified amines are formed by a substitution reaction between a polyamine and an epoxide, resulting in a multifunctional amine having a hydroxyl substituent. The use of these selectively modified amines in curing agents for epoxy resins improves the properties of the cured resin.

More specifically, the polyamides and amidoamine curing agents include the reaction product of (1) an amine component comprising at least one selectively modified multifunctional amine of structure 1:

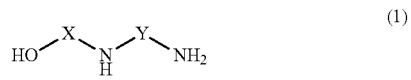

(1)

where X and Y are selected independently from C2 to C16 linear, cyclic, and branched alkyl, alkenyl, and alkaryl groups, or $(R1\text{-}NHR2)_m$, where m is 1 to 3, and R1 and R2 are alkylene groups of at least one C atom; and (2) a fatty acid component. Exemplary fatty acid components include at least one of monomer fatty acids, dimer fatty acids, trimer fatty acids, polymer fatty acids, esters of monomer, dimer, trimer, and polymer fatty acids and combinations thereof.

Another aspect of the disclosure includes a method for forming a polyamide curing agent composition which is the reaction product of an amine component comprising selectively modified amines and a fatty acid. More specifically, the method includes providing an amine component comprising at least one selectively modified multifunctional amine of structure 1:

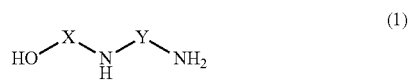

(1)

where X and Y are selected from C2 to C16 linear, cyclic, and branched alkyl, alkenyl, and alkaryl groups, or (R1-NH—R2)$_m$, where m is 1 to 3, and R1 and R2 are alkylene groups of at least one C atom; providing a fatty acid component; and reacting the amine component and fatty acid component to form the polyamide curing agent. Exemplary fatty acid components include at least one of monomer fatty acids, dimer fatty acids, trimer fatty acids, polymer fatty acids, esters of monomer, dimer, trimer, and polymer fatty acids and combinations thereof.

Another aspect of the present disclosure includes an amine-epoxy composition comprising the reaction product of 1) a curing agent composition; and 2) an epoxy composition comprising at least one multi-functional epoxy resin. The curing agent composition includes the reaction product of (1) an amine component comprising at least one selectively modified multi-functional amine of structure 1:

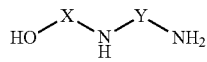
(1)

where X and Y are selected independently from C2 to C16 linear, cyclic, and branched alkyl, alkenyl, and alkaryl groups, or (R1-NH—R2)$_m$, where m is 1 to 3, and R1 and R2 are alkylene groups of at least one C atom; and (2) a fatty acid component. Exemplary fatty acid components include at least one of monomer fatty acids, dimer fatty acids, trimer fatty acids, polymer fatty acids, esters of monomer, dimer, trimer, and polymer fatty acids and combinations thereof.

Other features and advantages of the present invention will be apparent from the following more detailed description of the preferred embodiment, which illustrates, by way of examples, the principles of the invention.

DETAILED DESCRIPTION OF THE INVENTION

The following definitions and abbreviations are provided to aid those skilled in the art in understanding the detailed description of the present invention. AHEW—amine hydrogen equivalent weight; D230 poly(alkylene oxide) from Huntsman Corp.; DETA—diethylenetriamine, AHEW=21; DGEBA—diglycidyl ether of bisphenol-A, EEW=182-192; EEW—epoxy equivalent weight; HEW—hydrogen equivalent weight; HMDA—hexamethylenediamine; IPDA—isophoronediamine, AHEW=143; PEHA—pentaethylenehexamine; PHR—parts per hundred weight resin; TEPA—tetraethylenepentamine; TETA—triethylenetetramine, AHEW=125; TOFA—tall oil fatty acid.

The present disclosure includes polyamide and amidoamine compositions prepared from amines comprising hydroxyalkyl polyamines, methods for making polyamide and amidoamine compositions, and methods for using polyamide and amidoamine compositions as curing agents. The present disclosure also includes polyamide and amidoamine cured epoxy compositions.

Selectively modified amines may be used with fatty acids to manufacture amidoamines and polyamides having improved properties compared to existing amidoamines and polyamides prepared entirely from unmodified amines. The selectively modified amine may be formed from a substitution reaction by reacting the amine with an epoxide. The use of these selectively modified amine compounds to form polyamide and amidoamine curing agents for epoxy resins improves the properties of the cured resin.

Exemplary polyamide curing agent compositions are formed as reaction products of at least one fatty acid and an amine component preferably comprising at least one selectively modified multifunctional amine. The curing agent is preferably formed from selectively modified amines as well as unmodified polyamines.

Amine Component

The amine component comprises at least one selectively modified multifunctional amine of structure (1):

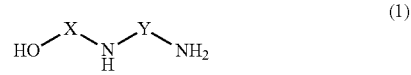
(1)

where X and Y are selected from: C2 through C16 linear, cyclic, and branched alkyl, alkenyl, and alkaryl groups, or (R1-NH—R2)$_m$, where m is 1 to 3, and R1 and R2 are alkylene groups of at least one C atom. Examples of suitable selectively modified multifunctional amines of structure (1) include compounds having a formula selected from formulas (2) through (13):

(2)

(3)

(4)

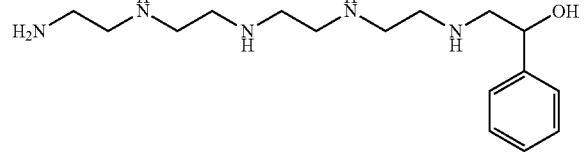
(5)

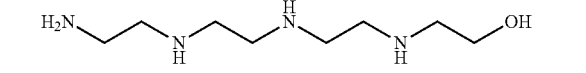
(6)

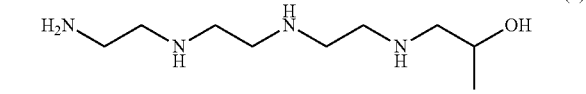
(7)

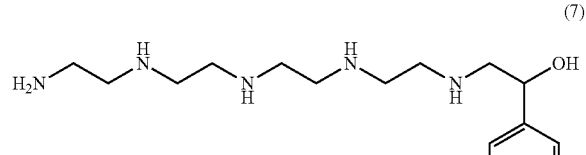
(8)

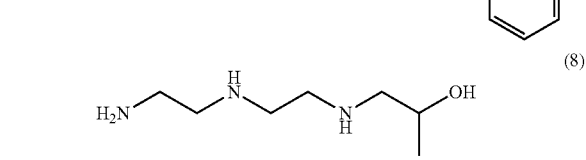

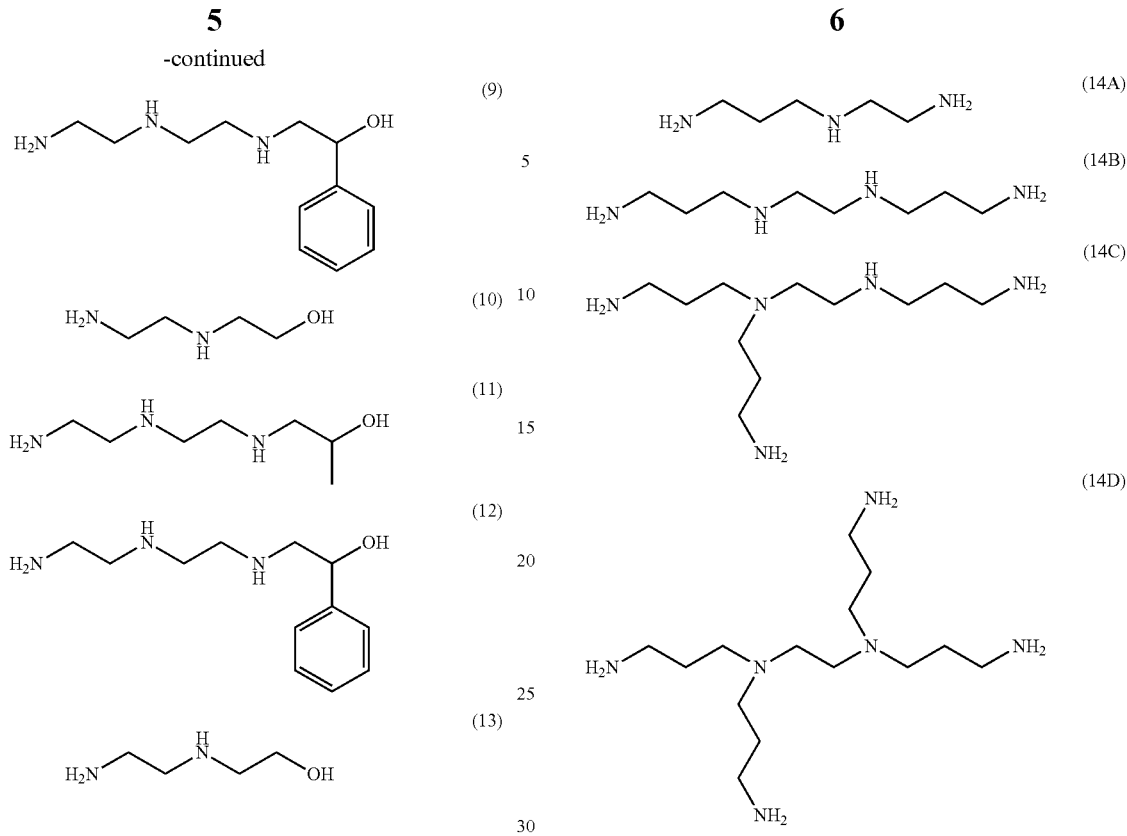

In order to create each selectively modified amine of the amine component, at least one polyamine, also referred to herein as an "unmodified polyamine" is reacted with at least one epoxide to form a multifunctional amine having a hydroxyl functional group. Suitable compounds for the at least one epoxide include, ethylene oxide and similar epoxides, including, but not limited to, propylene oxide, butylene oxide, pentene oxide, styrene oxide. The reaction between the at least one polyamine and at least one epoxide is preferably carried out near ambient temperature and pressure.

Preferably, the at least one polyamine is reacted with the at least one epoxide at a polyamine to epoxide ratio of from about 0.5:1 to about 2:1 on a molar basis, and more preferably, between about 1.2:1 and about 1.3:1 on a molar basis. The reaction is preferably carried out at temperatures from about 25° C. to about 120° C. over a time period ranging from about 1 to about 8 hours.

Each unmodified polyamine is preferably a compound having the structure (14):

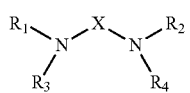

(14)

where R1 is CH2CH2CH2NH2; R2, R3 and R4 are each independently selected from H or CH2CH2CH2NH2; and X is CH2CH2 or CH2CH2CH2. Preferably, no more than one of R2 and R3 are H.

Exemplary suitable unmodified polyamines for use in forming the selectively modified amine include one or more of the following structures (14A) through (14D):

By "selectively modified" it is meant that modification or substitution takes place on a primary amino group of the unmodified polyamine. That is, the degree of substitution of the amino group being selectively modified is preferably 1. For example, referring to formulas 14A-14D, the amino group that is the site for substitution with a C2 through C16 linear, cyclic, and branched alkyl, alkenyl, and alkaryl alcohol functionality is preferably a primary amino group, not a secondary or tertiary amino group.

In some applications, it is preferable for the unmodified polyamine to comprise a mixture of one or more of the amines shown in 14(A) through 14(D) and other unmodified polyamines, particularly polyethylene polyamines.

The unmodified polyamine is preferably a higher polyethylene polyamine. Examples of suitable unmodified polyamines include polyamines consisting of: an aliphatic polyamine such as diethylenetriamine (DETA), triethylenetetramine (TETA), teraethylenepentamine (TEPA), pentaethylenehexamine (PEHA), hexamethylenediamine (HMDA), N-(2-aminoethyl)-1, 3-propanediamine (N3-Amine), N, N'-1, 2-ethanediylbis-1, 3-propanediamine (N4-amine), or dipropylenetriamine; an arylaliphatic polyamine such as m-xylylenediamine (mXDA), or p-xylylenediamine; a cycloaliphatic polyamine such as 1,3-bisaminocyclohexylamine (1,3-BAC), isophorone diamine (IPDA), or 4,4'-methylenebiscyclohexanamine; an aromatic polyamine such as m-phenylenediamine, diaminodiphenylmethane (DDM), or diaminodiphenylsulfone (DDS); a heterocyclic polyamine such as N-aminoethylpiperazine (NAEP), or 3,9-bis (3-aminopropyl) 2, 4,8, 10-tetraoxaspiro (5,5)undecane; a polyalkoxypolyamine where the alkoxy group can be an oxyethylene, oxypropylene, oxy-1, 2-butylene, oxy-1, 4-butylene or co-polymers thereof such as 4,7-dioxadecane-1, 10-diamine, 1-propanamine, 3,3 (oxybis(2, 1-ethanediyloxy))bis(diaminopropylated diethylene glycol ANCAMINE 1922A), poly (oxy(methyl-1, 2-ethanediyl)), alpha-(2-aminomethylethyl) omega-(2-aminomethylethoxy) (JEFFAMINE D 230, D-400), triethyleneglycoldiamine and oligomers (JEFFAMINE XTJ-504, JEFFAMINE XTJ-512), poly(oxy(methyl-1, 2-ethanediyl)), alpha, alpha'-(oxydi-2, 1-ethanediyl)bis(omega-(aminomethylethoxy)) (JEFFAMINE XTJ-511),bis(3-aminopropyl)polytetrahydrofuran 350, bis(3-aminopropyl) polytetrahydrofuran 750, poly(oxy (methyl-1, 2-ethanediyl)), a-hydro-w-(2-aminomethylethoxy)ether with 2-ethyl-2-(hydroxymethyl)-1, 3-propanediol (3:1) (JEFFAMINET-403), and diaminopropyl dipropylene glycol. JEFFAMINE is a registered trademark of Huntsman Petrochemical LLC.

Particularly suitable unmodified polyamines include polyamines consisting of diethylenetriamine (DETA), triethylenetetramine (TETA), 1,3-bisaminocyclohexyl amine (1,3-BAC), isophoronediamine (IPDA), N-aminoethylpiperazine (NAEP), 4,7-dioxadecane-1, 10-diamine, 1-propanamine, 3,3'-(oxybis(2, 1-ethanediyloxy))-(ANCAMINE 1922A), poly(oxy(methyl-1, 2-ethanediyl)), alpha-(2-aminomethylethyl)omega-(2-aminomethylethoxy (JEFFAMINE D 230, D-400), triethylene glycol diamine (JEFFAMINE XTJ-504), and poly(oxy(methyl-1, 2-ethanediyl))alpha, alpha'-(oxy(di-2,1-ethanediyl))bis(omega-(aminomethylethoxy)). (JEFFAMINE XTJ-511) or mixture thereof.

In at least one application, the unmodified polyamine preferably consists essentially of TETA. In at least one other application, the unmodified polyamine preferably consists essentially of polyalkylenepolyamines.

The amine component preferably comprises amines which have been selectively modified as described above, and preferably unmodified polyamines. Selectively modified amines preferably comprise from about 20% to about 100% by weight of the amine component, more preferably from about 20% to about 40% by weight. The inclusion of unmodified polyamines in the amine component serves to adjust the HEW, reduce the cost of the system, and, in some cases, improve the chemical resistance for the protection of substrates, such as steel.

Suitable unmodified polyamines for the portion of the amine component that is unmodified (i.e. not reacted with an epoxide prior to reacting with the fatty acid) include diethylenetriamine (DETA), triethylenetetramine (TETA), teraethylenepentamine (TEPA), pentaethylenehexamine (PEHA), hexamethylenediamine (HMDA), N-(2-aminoethyl)-1, 3-propanediamine (N-Amine), N, N'-1, 2-ethanediylbis-1, 3-propanediamine (N4-amine), or dipropylenetriamine; an arylaliphatic polyamine such as m-xylylenediamine (mXDA), or p-xylylenediamine; a cycloaliphatic polyamine such as 1,3-bisaminocyclohexylamine (1,3-BAC), isophorone diamine (IPDA), or 4,4'-methylenebiscyclohexanamine; an aromatic polyamine such as m-phenylenediamine, diaminodiphenylmethane (DDM), or diaminodiphenylsulfone (DDS); a heterocyclic polyamine such as N-aminoethylpiperazine (NAEP), or 3,9-bis(3-aminopropyl)2,4,8, 10-tetraoxaspiro (5,5)undecane; a polyalkoxypolyamine where the alkoxy group can be an oxyethylene, oxypropylene, oxy-1, 2-butylene, oxy-1, 4-butylene or co-polymers thereof such as 4,7-dioxadecane-1, 10-diamine, 1-propanamine, 3,3'-(oxybis (2, 1-ethanediyloxy))bis(diaminopropylated diethylene glycol ANCAMINE1922A),poly(oxy(methyl-1, 2-ethanediyl)), alpha-(2-aminomethylethyl)omega-(2-aminomethylethoxy) (JEFFAMINE D 230, D-400), triethyleneglycoldiamine and oligomers (JEFFAMINE XTJ-504, JEFFAMINE XTJ-512), poly(oxy(methyl-1, 2-ethanediyl)), alpha, alpha'-(oxydi-2, 1-ethanediyl)bis(omega-(aminomethylethoxy)) (JEFFAMINE XTJ-511), bis(3-aminopropyl)polytetrahydrofuran 350, bis(3-aminopropyl)polytetrahydro furan 750, poly(oxy (methyl-1, 2-ethanediyl)), a-hydro-w-(2-aminomethylethoxy)ether with 2-ethyl-2-(hydroxymethyl)-1, 3-propanediol (3:1) (JEFFAMINE T-403), and diaminopropyldiaminopropyl dipropylene glycol.

Particularly suitable unmodified polyamines for the portion of the amine component that is unmodified include diethylenetriamine (DETA), triethylenetetramine (TETA), 1,3-bisaminocyclohexylamine (1,3-BAC), isophoronediamine (IPDA),N-aminoethylpiperazine (NAEP), 4,7-dioxadecane-1, 10-diamine,l-prop anamine, 3,3'-(oxybis(2,1-ethanediyloxy))bi s-(ANCAMINE 1922A), poly(oxy(methyl-1, 2-ethanediyl)), alpha-(2-aminomethyl ethyl) omega-(2-aminomethylethoxy(JEFFAMINE D 230, D-400), triethylene glycol diamine (JEFFAMINE XTJ-504), and poly(oxy(methyl-1, 2-ethanediyl)) alpha, alpha'-(oxy(di-2, 1-ethanediyl))bis(omega-(aminomethylethoxy)). (JEFFAMINE XTJ-511) or mixture thereof.

Fatty Acid Component

The fatty acid component preferably comprises at least one fatty acid that has been polymerized under pressure and distilled to remove a majority of unreacted fatty mono-acids. "Dimerized" or "dimer" or "polymerized" fatty acid, as utilized herein, refers generally to polymerized acids obtained from unsaturated fatty acids. Examples of suitable unsaturated fatty acids include tall oil fatty acid (TOFA), soya fatty acid and cottonseed fatty acid. The dimer acid may also be further processed by, for example, hydrogenation, which reduces the degree of unsaturation and the color of the product.

The fatty acid component preferably comprises at least 50% dimeric acids and trimeric acids. The preferred ratio range of dimeric acids and trimeric acids will depend on, among other factors, processing conditions and the composition of the unsaturated acid feedstock.

Exemplary fatty acid components include dimer acids with a dimer content as measured by gas chromatography (GC) ranging from about 50 wt % to about 95 wt %, and a trimer acid content of from about 3 wt % to about 40 wt %, the remainder being monomeric fatty acids. However, as the amount of trimer acid is increased, it may be necessary to increase the amount of polyamine and/or the amount of fatty mono-acid to maintain a desired viscosity of the final product. The higher functionality of the trimeric fatty acids will lead to more branching and increase the molecular weight in the product, and may even gel the product, as will be appreciated by those skilled in the art. Esters of dimer acids, particularly the C1, to C4 alkyl esters, can also be employed in embodiments of the present disclosure.

Additional exemplary fatty acid components comprise a dimeric acid content of 75 wt % to 90 wt %, where the dimeric acid comprises at least one selected from the group of EMPOL 1018, EMPOL 1019, EMPOL 1029 and EMPOL 1022 (Cognis Corp.), HARIDIMER™ 250S (Harima M.I.D., Inc.), YONGLIN YLD-70 (Jiangsu Yonglin Chemical Oil Co.) and UNIDYME 18 (Arizona Chemical Co.). EMPOL is a registered trademark of Cognis Corporation. UNIDYME is a registered trademark of Union Camp Corporation.

Additional exemplary fatty acid components suitable for use in combination with the dimer acids include C8 to C20, preferably C16 to C20 monocarboxylic acids containing from 0 to about 4 units of unsaturation.

Additional exemplary fatty acid components include mixtures derived from triglycerides of natural products, such as babassu, castor, coconut, corn, cottonseed, grapeseed, hempseed, kapok, linseed, wild mustard, oiticica, olive, ouri-curi, palm, palm kernel, peanut, perilla, poppy seed, rapeseed, safflower, sesame, soybean, sugarcane, sunflower, tall, tea seed, tung, uchuba, or walnut oils. Pure fatty acids or mixtures of pure fatty acids, such as stearic, palmitic, oleic, linoleic, linolenic, etc. acids may also be employed, as can various esters of any of these fatty acids, particularly the C1 to C4 esters.

Also of utility is isostearic acid, also known as monomer acid. Monomer acid is the mostly C18 fatty mono-acid stream derived from the preparation of dimer acid. In one embodiment, the fatty acids blended with the dimer acids are tall oil fatty acid and soya fatty acid. If desired, other mono-functional and multifunctional carboxylic acids may be incorporated into the dimer acid portion of the reaction composition. In addition, other mono-functional or difunctional carboxylic acids of lower molecular weight or other multifunctional amines may be reacted with the modified amine component to provide specialized property enhancements.

In some applications, it is preferable to include lower molecular weight (poly) acids in the fatty acid component in order to reduce the amine hydrogen equivalent weight (HEW) which, in turn, will reduce the amount of polyamide or amidoamine needed to cure the epoxy.

Forming the Curing Agent

The amidoamine compounds of the curing agent preferably have the general structure of formula 15,

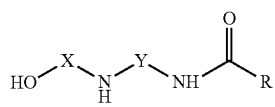

(15)

where R is an alkyl or aryl group of 1-30 carbon atoms. The polyamide compounds of the curing agent preferably have the general structure of formula 16, where A and B independently are aryl or alkyl groups of 1-30 carbon atoms.

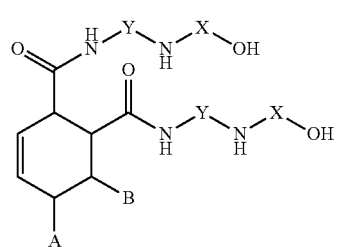

(16)

The polyamide or amidoamine curing agent is preferably formed by a reaction under heat. In one embodiment, the amine component and the fatty acid component are combined at temperatures ranging from about room temperature to about 250° C. at ambient pressure. A suitable ratio of reactants for the reaction include about a 1:1 ratio of a 1:1 molar ratio of fatty acid functionality to amine functionality. In addition, in formulations in which the fatty acid component includes monomeric fatty acids and dimeric fatty acids, the preferred fatty acid to selectively modified polyamide ratio is 1:1 of total acid to primary amine groups on a molecular basis.

The curing agent is preferably formed in a two-step reaction. Heat is supplied to raise the temperature as water is produced by the initial condensation reaction of the fatty acid and the amine to form an amine functional amide. At temperatures of about 200° C. and higher some of the amine functional amides cyclize yielding additional water and imidazoline and some tetrahydropyrimidines. Heating is continued until an amount of water is removed that will yield a product with the desired amide and imidazoline or tetrahydropyrimidine content. The amount of water is determined by weight. The progress of the reaction is preferably monitored by using infrared spectroscopy (IR) to measure the imidazoline to amide ratio. The reaction is continued until substantially all the carboxylic acid groups of the fatty acid component are reacted. At that stage some imidazoline or tetrahydropyrimidine has formed, up to 50 mole %. Preferably, when the endpoint of the reaction is reached, the imidazoline to amide ratio is between about 2:1 and about 3.5:1. More preferably, the ratio is between about 2.3:1 and about 3.2:1. Most preferably the ratio is about 3:1.

The cyclization reaction is shown below for tetrahydropyrimidines in reaction (17).

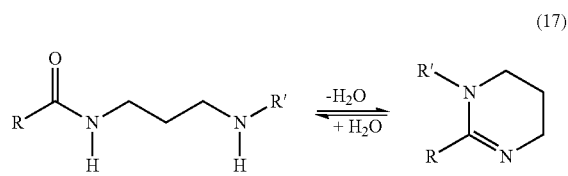

(17)

Optionally, a vacuum can be applied to the reaction vessel, particularly in the later stages of the process to aid in the removal of water from the mixture. Preferably the later stage of the process is when the reaction has progressed to about 75% of the targeted imidazoline to amide ratio. To reduce foaming, which can be a problem particularly under vacuum conditions, small amounts of defoamers may be added to the polyamide composition. Suitable defoamers include various acrylic copolymers containing 2-ethylhexyl acrylate as part of the copolymer composition, various polysiloxane copolymers, and the like.

Alkylation modification of the selectively modified polyamine results in a lower viscosity of the polyamide or amidoamine.

The curing agents of the present disclosure exhibit several desirable characteristics, including low viscosity, little or no induction time, a transparent mix with the epoxy resin, less carbamation (blushing) for thin film coating applications, increased cure speeds for low temperature cure and improved adhesion to the substrate on which it is applied.

Preferred viscosity ranges for the curing agents are from about 6000 MPa s up to about 100,000 MPa s, more preferably, from about 10,000 MPa s to about 15,000 MPa s. One particularly suitable range of viscosities is from about 8,000 MPa s to about 15,000 MPa s. In addition, the use of the curing agent described herein in epoxy composition may produce a film with little or no carbamation/blushing. Other advantages include faster dry time for polyamide curing agents and longer pot life for amidoamines.

Certain embodiments of exemplary amido amines may have long pot lives, for example, up to 30 hours. Certain embodiments of exemplary polyamides may have a thin film set time of about 7 hours. The high miscibility resulting from the use of polyamides is particularly suitable for coating applications such as primers, paints and the similar lower viscosity applications.

In addition, polyamides formed according to the present disclosure generally have shorter pot lives than amidoamines.

Multifunctional Epoxy Resin

Amine-epoxy compositions of the present disclosure comprise the reaction product of a curing agent composition and an epoxy composition comprising at least one multifunctional epoxy resin. Multifunctional epoxy resin, as used herein, describes compounds containing 2 or more 1, 2-epoxy groups per molecule. Epoxide compounds of this type are well known to those of skill in the art and are described in Y. Tanaka, "Synthesis and Characteristics of Epoxides", in C. A. May, ed., Epoxy Resins Chemistty and Technology (MarcelDekker, 1988), which is incorporated herein by reference.

One class of epoxy resins suitable for use in the present disclosure comprises the glycidyl ethers of polyhydric phenols, including the glycidyl ethers of dihydric phenols. Illustrative examples include, but are not limited to, the glycidyl ethers of resorcinol, hydroquinone, bis-(4-hydroxy-3, 5-difluorophenyl)-methane, 1,1-bis-(4-hydroxyphenyl)-ethane,2,2-bis-(4-hydroxy-3-methylphenyl)-propane, 2,2-bis-(4-hydroxy-3, 5-dichlorophenyl) propane, 2, 2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Additionally, advanced dihydric phenols of structure 18 also are useful in the present disclosure:

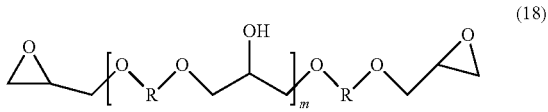

(18)

where m is an integer, and R is a divalent hydrocarbon radical of a dihydric phenol, such as those dihydric phenols listed above. Materials according to this formula can be prepared by polymerizing mixtures of a dihydric phenol and epichlorohydrin, or by advancing a mixture of a diglycidyl ether of the dihydric phenol and the dihydric phenol. While in any given molecule the value of m is an integer, the materials are invariably mixtures which can be characterized by an average value of m which is not necessarily a whole number. Polymeric materials with an average value of m between 0 and about 7 can be used in one aspect of the present disclosure.

In another aspect, epoxy novolac resins, which are the glycidyl ethers of novolac resins, can be used as multifunctional epoxy resins in accordance with the present disclosure. In yet another aspect, the at least one multifunctional epoxy resin is a diglycidyl ether of bisphenol-A (DGEBA), an advanced or higher molecular weight version of DGEBA, a diglycidyl ether of bisphenol-F, an epoxy novolac resin, or any combination thereof. Higher molecular weight versions or derivatives of DGEBA are prepared by the advancement process, where excess DGEBA is reacted with bisphenol-A to yield epoxy terminated products. The epoxy equivalent weights (EEW) for such products range from about 450 to 3000 or more. Because these products are solid at room temperature, they are often referred to as solid epoxy resins. DGEBA or advanced DGEBA resins are often used in coating formulations due to a combination of their low cost and generally high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of 174. Resins with EEW's between 250 and 450, also generally prepared by the advancement process, are referred to as semi-solid epoxy resins because they are a mixture of solid and liquid at room temperature. Generally, multi-functional resins with EEW's based on solids of about 160 to about 750 are useful in the present disclosure. In another aspect the multifunctional epoxy resin has an EEW in a range from about 170 to about 250. Depending upon the end-use application, it can be beneficial to reduce the viscosity of the compositions of the present disclosure by modifying the epoxy component. For example, the viscosity can be reduced to allow an increase in the level of pigment in a formulation or composition while still permitting easy application, or to allow the use of a higher molecular weight epoxy resin. Thus, it is within the scope of the present disclosure for the epoxy component, which comprises at least one multifunctional epoxy resin, to further comprise a mono-functional epoxide. Examples of monoepoxides include, but are not limited to, styrene oxide, cyclohexene oxide and the glycidyl ethers of phenol, cresols, tertbutylphenol, other alkyl phenols, butanol, 2-ethylhexanol, C4 to C14 alcohols, and the like, or combinations thereof. The multifunctional epoxy resin can also be present in a solution or emulsion, with the diluent being water, an organic solvent, or a mixture thereof.

Amine-Epoxy Compositions

To form an epoxy product or article of manufacture, the polyamide curing agent, or hardener, is combined with an epoxy resin, which is a polyepoxy compound containing about 2 or more 1,2-epoxy groups per molecule. Examples of epoxides are described in Y. Tanaka, "Synthesis and Characteristics of Epoxides", in C. A. May, ed. Epoxy Resins Chemistry and Technology (Marcel Dekker, 1988), and are incorporated by reference. Such combination of polyamide curing agent and epoxy resin composes a curable epoxy system.

Particularly suitable polyepoxy compounds are the diglycidyl ethers of bisphenol-A, the advanced diglycidyl ethers of bisphenol-A, the diglycidyl ethers of bisphenol-F, and the epoxy novolac resins.

Exemplary polyamides of the current disclosure are formulated with epoxy resins at stoichiometric ratios of epoxy groups to amine hydrogen ranging from about 1.5 to 1 to about 1 to 1.5. More preferred are ranges from 1.2 to 1 to 1 to 1.2.

Amide-Epoxy Coatings

Coatings prepared from polyamides of the current disclosure and epoxy resins can be formulated with a wide variety of ingredients well known to those skilled in the art of coating formulation, including solvents, fillers, pigments, pigment dispersing agents, rheology modifiers, thixotropes, flow and leveling aids, defoamers, etc. Mixtures of solvents will frequently be chosen so as to give the best evaporation rate profile for the system while maintaining solubility of the binder components. Suitable solvents include aromatics, aliphatics, esters, ketones, ethers, alcohols, glycols, glycol ethers, and the like. Particularly useful in the formulation are some level of ketones such as acetone, methyl ethyl ketone, methyl iso-amyl ketone, methyl propyl ketone, methyl amyl ketone, diacetone alcohol and the like, which can be used to improve pot life with little or no sacrifice in dry speed. If ester solvents are included in the formulation, it is usually necessary to formulate them in the package containing the epoxy resin, so as to minimize their reaction with the amine curing agent. Sometimes the epoxy resins used in the practice of this disclosure will be supplied in solvent cut versions, and likewise, it may be of value to use the polyamides of the current disclosure, or other curing agents used in combination with these polyamides, as solvent-cut versions.

Coatings of this disclosure can be applied by any number of techniques including spray, brush, roller, paint mitt, and the like. Numerous substrates are suitable for application of coatings of this disclosure with proper surface preparation, as is well understood in the art. Such substrates include but are not limited to many types of metal, particularly steel and aluminum, as well as concrete and ceramics.

Coatings of this disclosure can be applied and cured at ambient temperatures ranging from about 0° C. to about 50° C., with temperatures of 10° C. to 40° C. preferred. If desired, these coatings can also be force cured at temperatures up to 150° C. or more.

Optional Additives and Process Steps

Compositions of the present disclosure can be used to produce various articles of manufacture. Depending on the requirements during the manufacturing of or for the end-use application of the article, various additives can be employed in the formulations and compositions to tailor specific properties. These additives include, but are not limited to, solvents (including water), accelerators, plasticizers, fillers, fibers such as glass or carbon fibers, pigments, pigment dispersing agents, rheology modifiers, thixotropes, flow or leveling aids, surfactants, defoamers, biocides, or any combination thereof. It is understood that other mixtures or materials that are known in the art can be included in the compositions or formulations and are within the scope of the present disclosure.

Polyamides of the current disclosure may be modified with a portion of monofunctional epoxide. In this way viscosity is further reduced, which may be advantageous in certain cases, such as for example to increase the level of pigment in a formulation while still allowing easy application, or to allow the use of a higher molecular weight epoxy resin. Examples of useful monoepoxides include styrene oxide, cyclohexene oxide and the glycidyl ethers of phenol, the cresols, tert-butylphenol and other alkyl phenols, butanol, 2-ethyl-hexanol and C8 to C14 alcohols and the like.

It is also possible to modify the polyamides of the current disclosure by reacting a modest portion of the amine hydrogen with di functional and mono functional epoxy resins such as those described above. This is a common practice well known to those skilled in the art, and generally referred to as an "adduction". By adducting with difunctional and monofunctional epoxy resins it is possible to improve the compatibility of the polyamide with epoxy resin and thereby reduce problems such as blush, carbamation and exudation as described above, and to increase pot life. On the other hand, such modification tends to increase viscosity, particularly in the case of difunctional epoxy resins, and may in some cases also decrease the rate of cure. Particularly useful epoxy resins for adduction include the diglycidyl ethers of bisphenol-A, the advanced diglycidyl ethers of bisphenol-A, the diglycidyl ethers of bisphenol-F, styrene oxide, cyclohexene oxide and the glycidyl ethers of phenol, the cresols, tert-butylphenol and other alkyl phenols, butanol, 2-ethylhexanol, and C8 to C14 alcohols and the like. It is also possible to accomplish a modest level of adduction by mixing the amine and epoxy components and allowing them to stand for some period of time known as an induction period to those skilled in the art, normally 15 to 60 minutes, before application.

In some circumstances, it may be advantageous to incorporate so-called accelerators for the epoxy-amine curing reaction in formulations based on polyamides of the current disclosure. Such accelerators are described in H. Lee and K. Neville, Handbook of Epoxy Resins, McGraw-Hill, New York, 1967. Suitable accelerators include various organic acids, alcohols, phenols, tertiary amines, hydroxylamines, and the like. Particularly useful accelerators include benzyl alcohol, phenol, alkyl substituted phenols such as nonylphenol, octylphenol, t-butylphenol, cresol and the like, bisphenol-A, salicylic acid, dimethylaminomethylphenol, bis(dimethylaminomethyl)phenol, and tris(dimethylaminomethyl)phenol. Normally, such accelerators are used at levels of 10% or less based on the total weight of binder, and more usually at levels of less than 5%. In some circumstances, it may be advantageous to incorporate plasticizers for the epoxy-amine network in formulations based on polyamides of the current disclosure. This is particularly useful in cases where, in the absence of such a plasticizer, the glass transition temperature, Tg, of the composition significantly exceeds the ambient temperature before the degree of reaction necessary to meet certain requirements such as solvent and chemical resistance and tensile strength has been achieved. Such plasticizers are well known to those skilled in the art, and are described more fully in D. F. Cadogan and C. J. Howick, 'Plasticizers', in J. I. Kroschwitz, ed., Kirk-Othmer Encyclopedia of Chemical Technology, 4' Ed., Wiley, New York, 1996, Vol. 19, pp. 258-290. Particularly useful plasticizers include benzyl alcohol, nonylphenol, and various esters of phthalic acid. The ester plasticizers would normally be incorporated in the same package as the epoxy resin to minimize reaction with the amine curing agent. Another particularly useful class of plasticizers is hydrocarbon resins, which include toluene-formaldehyde condensates such as EPODIL L, xylene-formaldehyde condensates such as NIKANOL Y50, coumarone-indene resins, and many other hydrocarbon resin modifiers well know to those skilled in the art. EPODIL is a registered trademark of Evonik Corp. NIKANOL is a registered trademark of Mitsubishi Gas Chemical Company, Inc.

Articles of Manufacture

The present disclosure also is directed to articles of manufacture comprising the compositions disclosed herein. For example, an article can comprise an amidoamine-epoxy composition which comprises the reaction product of a curing agent composition and an epoxy composition. The curing agent composition can comprise the contact product of at least one of the amidoamines having 2 or more active amine hydrogens. The said product can be further formulated with polyfunctional amines, catalysts; accelerators, reactive or non-reactive diluents. The epoxy composition can comprise at least one multifunctional epoxy resin. Optionally, various additives can be present in the compositions or formulations used to produce fabricated articles, dependent upon the desired properties. These additives can include, but are not limited to, solvents (including water), accelerators, plasticizers, fillers, fibers such as glass or carbon fibers, pigments, pigment dispersing agents, rheology modifiers, thixotropes, flow or leveling aids, surfactants, defoamers, biocides, or any combination thereof.

Articles in accordance with the present disclosure include, but are not limited to, a coating, an adhesive, a construction product, a flooring product, or a composite product. Coatings based on these amine-epoxy compositions can be solvent free or can contain diluents, such as water or organic solvents, as needed for the particular application. Coatings can contain various types and levels of pigments for use in paint and primer applications. Amine-epoxy coating compositions comprise a layer having a thickness ranging from 40 to 400 μm (micrometer), preferably 80 to 300 μm, more preferably 100 to 250 μm, for use in a protective coating applied on to metal substrates. In addition, for use in a flooring product or a construction product, coating compositions comprise a layer having a thickness ranging from 50 to 10,000 μm, depending on the type of product and the required end-properties. A coating product that delivers limited mechanical and chemical resistances comprises a layer having a thickness ranging from 50 to 500 μm, preferably 100 to 300 μm; whereas a coating product such as, for example, a self-leveling floor that delivers high mechanical and chemical resistances comprises a layer having a thickness ranging from 1,000 to 10,000 μm, preferably 1,500 to 5,000 μm.

Numerous substrates are suitable for the application of coatings of this disclosure with proper surface preparation, as is well known to one of ordinary skill in the art. Such substrates include, but are not limited to, concrete and various types of metals and alloys, such as steel and aluminum. Coatings of the present disclosure are suitable for the painting or coating of large metal objects or cementitious substrates including ships, bridges, industrial plants and equipment, and floors. Coatings of this disclosure can be applied by any number of techniques including spray, brush, roller, paint mitt, and the like. In order to apply very high solids content or 100% solids coatings of this disclosure, plural component spray application equipment can be used, in which the amine and epoxy components are mixed in the lines leading to the spray gun, in the spray gun itself, or by mixing the two components together as they leave the spray gun. Using this technique can alleviate limitations with regard to the pot life of the formulation, which typically decreases as both the amine reactivity and the solids content increases. Heated plural component equipment can be employed to reduce the viscosity of the components, thereby improving ease of application.

Construction and flooring applications include compositions comprising the amine-epoxy compositions of the present disclosure in combination with concrete or other materials commonly used in the construction industry. Applications of compositions of the present disclosure include, but are not limited to, its use as a primer, a deep penetrating primer, a coating, a curing compound, and/or a sealant for new or old concrete, such as referenced in ASTM C309-97, which is incorporated herein by reference. As a primer or a sealant, the amine-epoxy compositions of the present disclosure can be applied to surfaces to improve adhesive bonding prior to the application of a coating. As it pertains to concrete and cementitious application, a coating is an agent used for application on a surface to create a protective or decorative layer or a coat. Crack injection and crack filling products also can be prepared from the compositions disclosed herein. Amine-epoxy compositions of the present disclosure can be mixed with cementitious materials such as concrete mix to form polymer or modified cements, tile grouts, and the like. Non-limiting examples of composite products or articles comprising amine-epoxy compositions disclosed herein in glass fiber reinforced composites, and other molded products.

In a particular embodiment, these curing agent compositions will have applicability in making epoxy filament-wound tanks, infusion composites such as windmill blades, aerospace adhesives, industrial adhesives, electronic components as well as other related applications. A composite is a material made of different substances, and in the case of resin, composites refer to resin impregnated systems where the resin is reinforced by the addition of reinforcing materials such as fillers and fibers for improving general properties of the resulting product. These materials work together but are not soluble in one another. In the present case, the binder component comprises the epoxy resin and epoxy curing agent(s). There are many types of composite applications such as prepregs, laminates, filament windings, braiding, pultrusion, wet lay and infusion composites. Resin infusion, or resin transfer, is a process by which resin is introduced to the composite mold, the reinforcement material having already been placed into the mold and closed prior to resin introduction. There are variations on this process such as those that are vacuum assisted. An advantage of the use of amidoamines of selectively modified polyamines in amine-epoxy compositions for making composites is the longer pot life and improved compatibility versus the amidoamines from polyamines like TEPA. These products have a long pot life but they lack the good miscibility with the epoxy and require consequent induction times before the systems become clear. These products are workable for filament winding and infusion applications. Using the (poly) amido amines for filament winding (pipes) is a very manual process with significant environmental, health and safety concerns (when TETA and epoxy resin is mixed, then the workers take cups of the mixture from a dispenser and manually pour them over the winding glass fibers and run their gloved hands along the pipe to run the liquid onto the winding pipe). With longer pot life the process could be automated with a bath. Also, the lower vapor pressure of the curing agent makes it safer to handle. The advantage in adhesives is again longer pot life, in this case so there is no skin-over before the parts are glued together, which is a major concern for large aircraft and windmill blades, when it takes a long time to place the adhesive beads across the entire part. If the adhesive that is put on the part first starts to cure or starts to blush over before the last of the adhesive is dispensed on the part, when the two pieces are pressed together there will be a weaker bond with the first bead.

EXAMPLES

The disclosure is further illustrated by the following examples, which are not to be construed as imposing limitations to the scope of this invention. Various other aspects, embodiment, modifications, and equivalents thereof which, after reading the description herein, may suggest themselves to one of ordinary skill in the art without departing from the spirit of the present invention or the scope of the appended claims.

Example 1, Synthesis of Amidoamines of Propylhydroxy Triethylenetetramine (Ancamine 1769) with TOFA An amine component comprising the selectively modified amine propylhydroxy triethylenetetramine (1.0 mole) is combined with a fatty acid component comprising TOFA (1.0 mole). The mixture is heated to 250° C. and held until water removal is completed while monitoring the ratio of imidazoline to amide by IR. When the IR ratio is about 2.5:1, the product is cooled and tested as a curing agent. The thin film set time, gel time, amine value and differential scanning calorimetry is determined when cured with the standard epoxy resin EPON 828 to form an amine-epoxy composition.

Example 2, Synthesis of Polyamide of Propylhydroxy Triethylenetetramine (Ancamine 1769) with Dimer Acid/TOFA An amine component comprising the selectively modified amine propylhydroxy triethylenetetramine (1.0 mole) is combined with a fatty acid component comprising dimer acid (0.45 mole) and TOFA (0.1 mole). The mixture is heated to 250° C. and held until water removal is completed while monitoring the ratio of imidazoline to amide by IR. When the IR ratio is about 3:1, the product is cooled and tested as a curing agent. The thin film set time, gel time, amine value and differential scanning calorimetry is determined when cured with the standard epoxy resin EPON 828 to form an amine-epoxy composition.

Example 3, Synthesis of Amidoamines from Hydroxyl Polyethylenepolyamine and TETA with TOFA An amine component comprising Berolamine XA-70 (100 g, 0.065 mole) was combined with a fatty acid component comprising TOFA (186.55 g, 0.65 mole). Berolamine XA-70 from Akzo Nobel comprises a mixture of an unmodified polyamine, TETA, and selectively modified amines, hydroxypolyethylene polyamines. The mixture was heated to 250° C. and held until water removal was completed while monitoring the ratio of imidazoline to amide by IR. When the IR ratio was about 3.1:1 the product was cooled and tested as an epoxy curing agent. The thin film set time, gel time, amine value and differential scanning calorimetry were determined when cured with the standard epoxy resin EPON 828 to form an amine-epoxy composition. The results of these studies are documented in Table 1.

Example 4, Synthesis of Polyamides from Hydroxyl Polyethylenepolyamine and TETA with a Mixture of Dimer Acid and TOFA An amine component comprising Berolamine XA-70 (100 g) was combined with a fatty acid component comprising dimer acid (160.72 g) and TOFA (17.22 g). The mixture was heated to 250° C. and held until water removal was completed while monitoring the ratio of imidazoline to amide by IR. When the IR ratio was about 2.3:1, the product was cooled and tested as an epoxy curing agent. The thin film set time, gel time, amine value and differential scanning calorimetry were determined when cured with the standard epoxy resin EPON 828 to form an amine-epoxy composition. The results of these studies are documented in Table 2.

Example 5, Synthesis of Polyamide from a Mixture of Berolamine XA-70 and TETA An amine component is formed comprising TETA (481 g) combined with Berolamine XA-70 (200.6 g) in a 2 L kettle reactor equipped with a N2 inlet, overhead mechanical stirrer, addition funnel and a distillation column. A fatty acid component comprising Dimer acid (1117.8 g) and TOFA (202.1 g) are added. The mixture is heated to 180° C. and held at that temperature until no more water is removed. The temperature is gradually raised to 250° C. while monitoring the IR for imidazoline/amide ratio. When the imidazoline/amide IR ratio is about 2.6:1 to 3.2:1, the reactor is cooled to room temperature. The product is discharged and mixed with epoxy resin (EPON 828) to form an amine-epoxy composition, which is tested for gel time, thin film set time and differential scanning calorimetry. The test results are compared with results for a standard polyamide made from TETA, dimer acid and TOFA. The results are documented in Table 3.

TABLE 1

Physical properties of amidoamines from TOFA and polyamines/hydroxyalkylamine blend.

| Sample | IR ratio Imidazoline/amide | Viscosity (mPa s) | Gel time (min) | TFST (h) | DSC Onset (° C.) | DSC ΔH | DSC $T_g$ | phr EPON 828 |
|---|---|---|---|---|---|---|---|---|
| TEPA/TOFA 1:1 mol. ratio | 2.1 | 279 | 385 | 23 | 23 | 330 | 60 | 56 |
| Example 3 Product | 1.95 | 210 | 338 | >24 | 71 | 293 | 31 | 77 |

TABLE 2

Physical properties of amidoamines from TOFA and polyamines/hydroxyalkylamine blend.

| Sample | IR ratio Imidazoline/amide | Viscosity (mPa s) | Gel time (min) | TFST (h) | DSC onset (° C.) | DSC ΔH | DSC $T_g$ | phr |
|---|---|---|---|---|---|---|---|---|
| TETA/Dimer acid/TOFA 0.65/0.28/0.06 mol. | 2.41 | 11,010 | 148 | 11 | 79 | 375 | 60 | 55 |
| Example 4 | 2.30 | 54,550 | 121 | 9 | 70 | 307 | 64 | 75 |

TABLE 3

| Sample | IR ratio Imidazoline/amide | Viscosity (mPa s) | Gel time (min) | TFST (h) | DSC onset (° C.) | DSC ΔH | DSC $T_g$ | phr |
|---|---|---|---|---|---|---|---|---|
| TETA/Dimer acid/TOFA 0.65/0.28/0.06 mol. | 2.41 | 11,010 | 148 | 11 | 79 | 375 | 60 | 55 |
| Example 5 | 2.89 | 11,400 | 136 | 9.75 | 80 | 315 | 75 | 55 |

What is claimed:

1. A curing agent comprising the reaction product of
   (1) an amine component comprising at least one selectively modified multifunctional amine, and
   (2) a fatty acid component comprising a mixture of tall oil fatty acid derived dimer acid and tall oil fatty acid;
   wherein the at least one selectively modified multifunctional amine comprises a compound having a structural formula selected from the group consisting of:

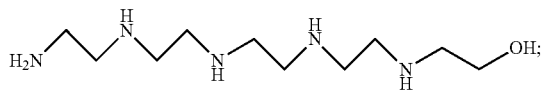

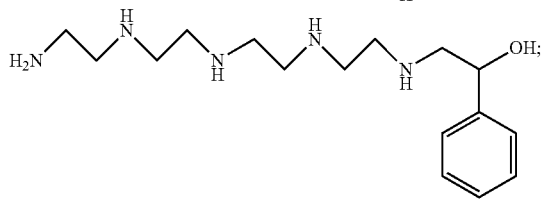

 and

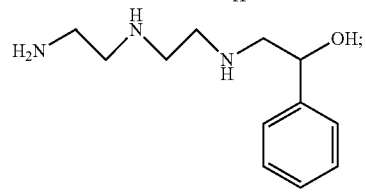

wherein the fatty acid component comprises at least one dimeric acid, at least one trimeric acid and at least one mono acid, wherein the dimeric acid comprises about 50 wt % to about 95 wt % of the fatty acid component, wherein the trimeric acid comprises about 3 wt % to about 40 wt % of the fatty acid component, and wherein the mono acid comprises less than 5 wt % of the fatty acid component; and wherein the curing agent has an imidazoline to amide ratio between about 2.3:1 and about 3.2:1.

2. The curing agent of claim 1, wherein a viscosity of the curing agent ranges from about 6000 MPa s to about 100,000 MPa s.

3. The curing agent of claim 1 wherein the at least one selectively modified multifunctional amine comprises hydroxyethyl polyethylenepolyamine.

4. The curing agent of claim 1 wherein the amine component comprises at least one unmodified polyalkylamine.

5. The curing agent of claim 1 wherein the fatty acid component comprises monocarboxylic acids containing from about 8 to about 20 carbon atoms and from about 0 to about 4 units of unsaturation.

6. The curing agent of claim 1 wherein the ratio of the fatty acid component to the amine component ranges from about 1:1 to about 2:1, on a molecular basis, for monomeric fatty acids.

7. The curing agent of claim 1 wherein the reaction product comprises amidoamine compounds having the general structure:

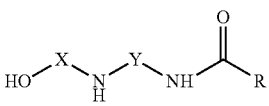

(15)

where R represents an alkyl or aryl group of 1-30 carbon atoms, and where X and Y are independently selected from $(R1-NH—R2)_m$, where m=1 to 3, and R1, R2=alkylene groups of at least one C atom.

8. The curing agent of claim 1 wherein the reaction product comprises polyamide compounds having the general structure:

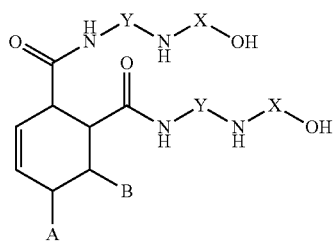

(16)

where A and B are, independently, alkyl or aryl groups of 1-30 carbon atoms, and where X and Y are independently selected from $(R1-NH—R2)_m$, where m=1 to 3, and R1, R2=alkylene groups of at least one C atom.

9. An amine-epoxy composition comprising the reaction product of:
   (1) the curing agent of claim 1; and
   (2) an epoxy composition comprising at least one multifunctional epoxy resin.

10. The amine-epoxy composition of claim 9, wherein the epoxy composition further comprises at least one polyepoxy compound.

11. The amine-epoxy composition of claim 10 wherein the at least one polyepoxy compound comprises at least one of the diglycidyl ethers of bisphenol-A, the advanced diglycidyl ethers of bisphenol-A, the diglycidyl ethers of bisphenol-F, and the epoxy novolac resins.

12. The amine-epoxy composition of claim 9, wherein the stoichiometric ratios of epoxy groups to amine hydrogen ranges from about 1.5 to 1 to about 1 to 1.5.

13. The amine-epoxy composition of claim 10, wherein the at least one polyepoxy compound comprises at least one dihydric phenol of the following structure:

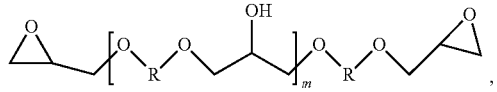

where m is 0 to 7, and R is a divalent hydrocarbon radical of a dihydric phenol.

14. An article of manufacture comprised of the amine-epoxy composition of claim 9.

15. A method for forming a curing agent, comprising:
(i) reacting (1) at least one selectively modified multifunctional amine, with (2) a fatty acid component comprising a mixture of tall oil fatty acid derived dimer acid and tall oil fatty acid, wherein the at least one selectively modified multifunctional amine comprises a compound having a structural formula selected from the group consisting of:

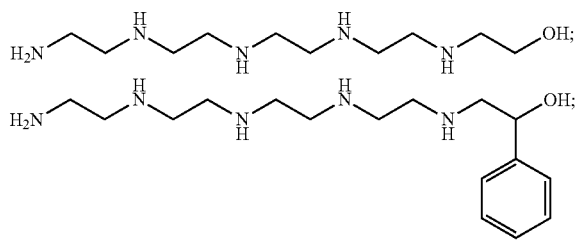

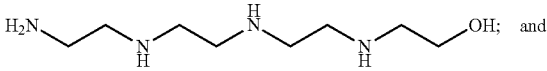

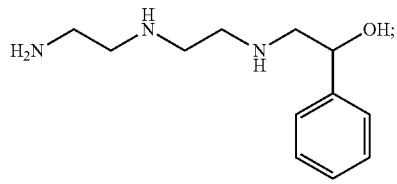

wherein the fatty acid component comprises at least one dimeric acid, at least one trimeric acid and at least one mono acid, wherein the dimeric acid comprises about 50 wt % to about 95 wt % of the fatty acid component, wherein the trimeric acid comprises about 3 wt % to about 40 wt % of the fatty acid component, and wherein the mono acid comprises less than 5 wt % of the fatty acid component; and wherein the curing agent has an imidazoline to amide ratio between about 2.3:1 and about 3.2:1.

16. The method of claim 15, further comprising adding a defoamer.

* * * * *